(12) United States Patent
Wilmotte et al.

(10) Patent No.: US 6,660,289 B1
(45) Date of Patent: Dec. 9, 2003

(54) DISINFECTING COMPOSITION BASED ON $H_2O_2$, ACIDS AND METAL IONS

(75) Inventors: Rémi Wilmotte, Chalons sur Vesles (FR); Bernard Lebeau, Colombes (FR); Jean-Pierre Irurzun, Le Plessis Trevise (FR); Françoise Marechal, La Garenne Colombes (FR)

(73) Assignee: Digol International LTD, Tortola (VG)

( * ) Notice: Subject to any disclaimer, the term of this patent is extended or adjusted under 35 U.S.C. 154(b) by 0 days.

(21) Appl. No.: 10/030,764

(22) PCT Filed: Apr. 25, 2000

(86) PCT No.: PCT/FR00/01093

§ 371 (c)(1),
(2), (4) Date: Oct. 23, 2001

(87) PCT Pub. No.: WO01/05233

PCT Pub. Date: Jan. 25, 2001

(30) Foreign Application Priority Data

Apr. 23, 1999 (FR) ............................................... 99 05186

(51) Int. Cl.⁷ .............................................. A01N 25/00
(52) U.S. Cl. ...................... 424/405; 424/401; 424/601; 424/604; 424/605; 424/616; 424/617; 424/618
(58) Field of Search ................................ 424/405, 401, 424/601, 605, 604, 616, 617, 618

(56) References Cited

U.S. PATENT DOCUMENTS

| | | | | |
|---|---|---|---|---|
| 3,035,698 A | | 5/1962 | Novak ........................ 209/235 |
| 3,702,298 A | | 11/1972 | Zsoldos, Jr. et al. .......... 210/62 |
| 3,907,991 A | | 9/1975 | Accetta ...................... 424/130 |
| 4,537,778 A | | 8/1985 | Clipper et al. ................ 424/53 |
| 4,659,564 A | * | 4/1987 | Cox et al. ..................... 424/65 |
| 4,980,152 A | | 12/1990 | Frazier et al. ................ 424/52 |
| 4,995,987 A | | 2/1991 | Whitekettle et al. ......... 210/754 |
| 5,017,295 A | | 5/1991 | Antelman .................... 210/764 |
| 5,078,902 A | | 1/1992 | Antelman .................... 210/764 |
| 5,098,582 A | * | 3/1992 | Antelman .................... 210/759 |
| 5,233,149 A | | 8/1993 | Killian et al. ............. 219/76.12 |
| 5,869,601 A | * | 2/1999 | Svoboda ..................... 528/480 |

FOREIGN PATENT DOCUMENTS

| | | |
|---|---|---|
| DE | 2659462 | 7/1978 |
| EP | 0087343 | 5/1985 |
| EP | 0193416 | 9/1986 |
| EP | 0233059 | 8/1987 |
| EP | 0370850 | 5/1990 |
| FR | 2321301 | 3/1977 |
| FR | 2321302 | 3/1977 |
| GB | 2189394 | 10/1987 |
| JP | 47-014756 | 9/1969 |
| JP | 9-202983 | 8/1997 |
| WO | 94/24863 | 11/1994 |
| WO | 96/18301 | 6/1996 |

* cited by examiner

*Primary Examiner*—Thurman K. Page
*Assistant Examiner*—Liliana Di Nola-Baron
(74) *Attorney, Agent, or Firm*—Ostrolenk, Faber, Gerb & Soffen, LLP

(57) ABSTRACT

The invention concerns an oxidising aqueous composition useful in particular for disinfection, hygiene and depollution purposes, and for surface treatment (particularly a metal surface to be stripped and/or passivated), and said composition, containing in water hydrogen peroxide, a $RCO_2H/RCO_3H$ mixture (wherein R is a $C_1$–$C_6$ aliphatic radical with linear or branched hydrocarbon chain, saturated or unsaturated), a stabilising agent which is an acid and, as the case may be, $Ag^+$ ions. The invention is characterised in that it contains ions of at least one metal M which are ions of $Ag^{II}$, $Ag^{III}$, $V^V$, $Nb^V$, $Ta^V$, $Mo^{VI}$, $W^{VI}$, $Co^{III}$, $In^{III}$ or $Tl^{III}$. Advantageously, said composition can be in gel form. The invention also concerns the method for preparing said composition.

12 Claims, No Drawings

DISINFECTING COMPOSITION BASED ON H₂O₂, ACIDS AND METAL IONS

FIELD OF THE INVENTION

The present invention concerns, as a novel industrial product, an aqueous composition, in particular in gel form, based on $H_2O_2$, acids and $Ag^{II}$, $Ag^{III}$, $V^V$, $Nb^V$, $Ta^V$, $Mo^{VI}$, $W^{VI}$, $Co^{III}$, $In^{III}$ or $Tl^{III}$ ions. The invention also relates to a preparation process, in particular when said ions are $Ag^{2+}$, and to the use of this composition in the field of disinfection, hygiene and/or decontamination, on the one hand, and in the field of surface treatment (in particular cleaning, stripping and/or passivation), on the other hand.

PRIOR ART

The closest prior art consists of patent document WO-A-96/18301. Before the publication of this document, aqueous disinfecting compositions, some containing hydrogen peroxide and a carboxylic acid/carboxylic peracid mixture of the type $RCO_2H/RCO_3H$ (in which R is essentially $CH_3$ or $CH_3CH_2$) (see in particular to this end EP-A-0 370 850, EP-A-0 193 416, EP-B-0 087 343, FR-A-2 321 301 and FR-A-2 321 302), and others containing hydrogen peroxide and $Ag^+$ ions (see in particular to this end U.S. Pat. No. 3,035,698 and GB-A-2 189 394), had already been proposed in the past, said aqueous disinfecting compositions being stabilized in each case with a strong acid (essentially $H_3PO_4$).

These prior aqueous disinfecting compositions, namely (i) those of the type $H_2O_2+RCO_2H/RCO_3H+H_3PO_4$ and (ii) those of the type $H_2O_2+Ag^++H_3PO_4$, are insufficient as regards their absence of efficacy on several strains of bacteria and molds, and in particular on the strains of *Penicillium verrucosum*.

A more recent and markedly more effective technique (in particular with regard to said strains of *Penicillium verrucosum* which were resistant to the two abovementioned types of aqueous disinfecting compositions) was described in the abovementioned WO-A-96/18301, which is incorporated herein by way of reference. According to WO-A-96/18301, the recommended technique uses an aqueous disinfecting, hygiene and decontaminating composition, which comprises, in water:

(A) $H_2O_2$, (B) an $RCO_2H/RCO_3H$ mixture (in which R is $CH_3$ or $CH_3CH_2$), (C) a silver component as a source of $Ag^+$ ions, and (D) a stabilizer (mainly $H_3PO_4$), Table IX of WO-A-96/18301 demonstrating the synergy of the aqueous composition containing the components A+B+C+D, compared with the aqueous compositions containing the components A+B+D and A+C+D.

It is found that the aqueous solution of A+B+C+D according to WO-A-96/18301 does not act quickly enough with regard to inhibiting or, better still, destroying microorganisms, such as bacteria, molds, viruses and microscopic algae, in particular by making their wall brittle, especially by degrading their biofilm, by perforating their wall or by preventing them from penetrating into the cells of the body or by protecting said cells against their toxins.

Moreover, the procedures described in GB-A-2 189 394 as regards the preparation of the concentrated aqueous silver solution (i.e. component C above) in the presence of $H_3PO_4$, on the one hand, and that of the resulting stabilized concentrated aqueous solution of silver and of hydrogen peroxide (i.e. the aqueous solution containing A+C+D), on the other hand, do not lead to the production of $Ag^{2+}$ ions or to that of $Ag^{3+}$ ions.

Specifically, GB-A-2 189 394, which recommends a process comprising:

mixing a strong mineral acid (pH<1.6) with a silver component (a silver salt or a silver complex), at a temperature of 50–60° C., the strong mineral acid/silver component molar ratio being greater than or equal to 1/1;

cooling the resulting mixture to a temperature of 25–30° C. and adding a stabilizing organic acid optionally with gelatin; and incorporating $H_2O_2$ into the resulting mixture, cites (see page 1, lines 46–50) silver (I) compounds which give $Ag^+$ ions in strong acid medium, these compounds are silver (I) salts and a silver (I) complex salt, namely $AgNaCl_2$, on the one hand, and silver (II) and (III) compounds which are soluble only in basic medium, these compounds are silver (II) and (III) oxides which, in strong acid medium, mainly give metallic silver in fine, on the other hand.

More specifically, the silver (I), (II) and (III) oxides give rise, in acid medium, to the following reactions, in which s denotes a solid product:

 (1)

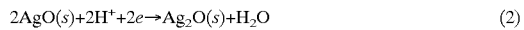 (2)

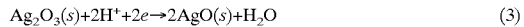 (3)

Since the direct placing in contact (i.e. without a strong acid stabilizer) of $H_2O_2$ and of a silver component is liable to cause an explosion, a process different from that recommended by GB-A-2 189 394 should be used to obtain the $Ag^{2+}$ ions that are useful according to the present invention.

For the same reasons, the procedures described in WO-A-96/18301 do not allow the oxidation in acid medium of silver (I) to silver (II) according to the reaction:

It is known that, according to U.S. Pat. Nos. 5,017,295 and 5,078,902, $Ag^{2+}$ ions have been presented as being more active as bactericidal agents than $Ag^+$ ions. Now, it is found that the procedures given in these two documents do not promote the production of $Ag^{2+}$ or $Ag^{2+}+Ag^{3+}$ ions since, with regard to reaction (2) above, the silver (II) oxide gives in acid medium a precipitate of silver (I) oxide. Thus, the reactions outlined in Example 1 of U.S. Pat. No. 5,017,295 and in Examples 1 and 2 of U.S. Pat. No. 5,078,902, namely:

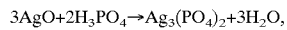

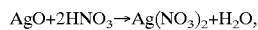

and

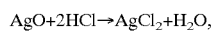

cannot take place. Furthermore, by reproducing the other method for obtaining $Ag^{2+}$ ions indicated in Example 2 of U.S. Pat. No. 5,078,902, which comprises the dissolution of AgO in alkaline medium, followed by the addition of an oxidizing source [i.e. oxone ($Na_2O_2$)] which can give hydrogen peroxide [this addition is carried out in alkaline medium (i.e. under conditions in which $H_2O_2$ intervenes as the reducing agent)], the resulting concentration of $Ag^{2+}$ ions is very low, such that the redox potential of the aqueous solution containing $Ag^+$ and $Ag^{2+}$ is always less than 650 mV (at 298 K). Thus, according to U.S. Pat. Nos. 5,017,295 and 5,078,902, the beneficial effects as stated for the $Ag^{2+}$ ions cannot be manifested.

Finally, U.S. Pat. No. 3,702,298 proposes the use of $Ag^{3+}$ ions as a germicidal means. However, the mixture $Ag^+ + Ag^{2+} + Ag^{3+}$ effectively obtained has a redox potential ranging from 0.15 mV to 0.4 mV, which is markedly lower than that desired according to the present invention which is greater than 1000 mV.

It is also known that molybdenum intervenes in human beings and warm-blooded animals as a coenzyme for the detoxifying enzymes located in the liver, such as xanthine oxidase, aldehyde oxidase and sulfite oxidase. Mo is essential for converting purine bases into uric acid, and it promotes the intestinal absorption of iron and the retention of fluorine in the body.

It is also known from U.S. Pat. No. 4,995,987 that molybdate and tungstate ions have been proposed, as agents for inhibiting the growth of sulfate-reducing bacteria, in combination with antimicrobial agents. Document U.S. Pat. No. 4,995,987 neither describes nor suggests the subject of the present invention.

In the field of treating metal surfaces, in particular to strip and/or passivate them, it is known that the conventional oxidizing means, such as chromic acid, chromates and nitric acid, are considered as being products that are harmful to the environment.

U.S. Pat. No. 4,537,778 moreover discloses an aqueous mouthwash or oral rinse composition which comprises 0.5–5% by weight of $H_2O_2$, 3–15% by weight of ethanol, 0.5–2% by weight of a nonionic and water-soluble surfactant of the polyoxyethylenated polyoxypropylene glycol type, 0.3–2% by weight of a nonionic and water-soluble surfactant of the type such as a $C_{10}-C_{18}$ fatty acid monoester with polyoxyethylenated sorbitol, a sweetener and a fragrance. This composition may be produced in the form of a paste or a gel by means of a thickener or a gelling agent, respectively. The gelling agent proposed is a gum (xanthan gum or guar gum), a carboxylic interpolymer described in U.S. Pat. No. 2,798,053 or a polyol of the PLURONIC® type comprising 70% to 20% of hydrophobic groups and 30% to 80% of hydrophilic groups, the preferred gelling agent being PLURONIC® 127 (see column 4, lines 28–29, column 5, lines 34 and 49, and column 6, lines 5–6). Now, it is found that such a gelling agent, which is of the organic polymer type, is degraded more or less quickly (within the space of a few minutes to a few days) by oxidizing compositions of high redox potential (in particular a redox potential of greater than or equal to 800 mV).

Finally, DE-A-2 659 462 discloses a pharmaceutical composition containing a specific silica gel, namely a silicic acid hydrogel which is usually used in the pharmaceutical field but has never been used under highly oxidizing conditions.

Finally, the prior art neither describes nor suggests the effective use of ions containing a metal with a degree of oxidation close to (in the particular case of $Ag^{II}$) or equal to (in the case of $Ag^{III}$, $V^V$, $Nb^V$, $Ta^V$, $Mo^{VI}$, $W^{VI}$, $Co^{III}$, $In^{III}$ or $Tl^{III}$) its maximum value, in a disinfecting composition or a composition for treating surfaces.

AIM OF THE INVENTION

It is desired, on the one hand, to overcome the above-mentioned drawbacks of the prior art, and, on the other hand, to provide a novel technical solution which is effective and unexpected when compared with the teaching of the prior art.

According to a first aspect of the invention, it is proposed to provide a novel technical solution to the problem of disinfection and/or of treating surfaces, which is more effective as regards the speed of action than the technical solution recommended by WO-A-96/18301.

According to a second aspect, it is proposed to provide a novel technical solution which has long-lasting action in order to obtain a persistence of the activity over a longer period of time, in particular when the surface to be treated is inclined or vertical.

SUBJECT OF THE INVENTION

The novel technical solution according to the invention for achieving the aforementioned aim is based on the use of specific metal ions, namely $Ag^{II}$, $Ag^{III}$, $V^V$, $Nb^V$, $Ta^V$, $Mo^{VI}$, $W^{VI}$, $Co^{III}$, $In^{III}$ or $Tl^{III}$ ions.

Thus, an aqueous oxidizing composition (I) is recommended, which is useful in particular in the field of disinfection, hygiene and decontamination, on the one hand, and in the field of treating a metal surface (in particular for cleaning, stripping and/or passivating it) or a nonmetal surface (in particular a plastic or ceramic surface, especially for cleaning and/or stripping it), on the other hand, said composition, which contains, in water, hydrogen peroxide, an $RCO_2H/RCO_3H$ mixture (in which R is a $C_1-C_6$ aliphatic residue containing a linear or branched, saturated or unsaturated hydrocarbon chain) and a stabilizer which is a strong acid and, where appropriate, $Ag^+$ ions, being characterized in that it contains ions of at least one metal M which are $Ag^{II}$, $Ag^{III}$, $V^V$, $Nb^V$, $Ta^V$, $Mo^{VI}$, $W^{VI}$, $Co^{III}$, $In^{III}$ or $Tl^{III}$ ions, the source L, which gives $Ag^{II}$ ions or $Ag^{II} + Ag^{III}$ ions, being such that, starting with 100 g of silver (i.e. 157 g of $AgNO_3$) and 1 liter of demineralized water, the concentration of $Ag^+ + Ag^{2+}$ or $Ag^+ + Ag^{2+} + Ag^{3+}$ ions in the resulting solution gives a redox potential of greater than 1000 mV.

More specifically, the composition (I) according to the invention is characterized in that it contains, in water:

(A) $H_2O_2$;
(B) an $RCO_2H/RCO_3H$ mixture (in which R is a $C_1-C_6$ aliphatic residue containing a linear or branched, saturated or unsaturated hydrocarbon-based chain;
(C) metal ions from a source L and chosen from the set consisting of:
  (1) ions of a metal M which are $Ag^{II}$, $Ag^{III}$, $V^V$, $Nb^V$, $Ta^V$, $Mo^{VI}$, $W^{VI}$, $Co^{III}$, $In^{III}$ or $Tl^{III}$ ions,
  (2) combinations of $Ag^+$ ions and of ions of said metal M, and
  (3) mixtures thereof;
  the source L, which gives $Ag^{II}$ ions or $Ag^{II} + Ag^{III}$ ions, being such that, starting with 100 g of silver (i.e. 157 g of $AgNO_3$) and 1 liter of demineralized water, the concentration of $Ag^+ + Ag^{2+}$ or $Ag^+ + Ag^{2+} + Ag^{3+}$ ions in the resulting solution gives a redox potential of greater than 1000 mV; and
(D) a stabilizer which is an acid.

This composition may be prepared according to a method which is known per se. The process which is recommended herein comprises the steps consisting in:

(a) using an aqueous solution of a source L giving metal ions chosen from the set consisting of
  (1) ions of a metal M which are $Ag^{II}$, $Ag^{III}$, $V^V$, $Nb^V$, $Ta^V$, $Mo^{VI}$, $W^{VI}$, $Co^{III}$, $In^{III}$ or $Tl^{III}$ ions, (2) combinations of $Ag^+$ ions and of ions of said metal M, and (3) mixtures thereof;

the source L, which gives $Ag^{II}$ ions or $Ag^{II}+Ag^{III}$ ions, being such that, starting with 100 g of silver (i.e. 157 g of $AgNO_3$) and 1 liter of demineralized water, the concentration of $Ag^++Ag^{2+}$ or $Ag^++Ag^{2+}+Ag^{3+}$ ions in the resulting solution gives a redox potential of greater than 1000 mV;

(b) introducing the stabilizer into said solution;

(c) introducing said resulting solution thus obtained into aqueous hydrogen peroxide solution or introducing the aqueous hydrogen peroxide solution into said resulting solution;

(d) introducing into the resulting solution thus obtained an acidic substance which is $RCO_3H$, $RCO_2H$ or a mixture thereof $RCO_3H+RCO_2H$ in which R is defined as indicated above;

(e) leaving the resulting solution thus obtained to stand until the equilibrium $H_2O_2+RCO_2H \Leftrightarrow H_2O+RCO_3H$ is established; and (f) making up to 100% by weight with water.

The process for preparing a composition according to the invention which contains $Ag^{2+}$ ions and, where appropriate, $Ag^{3+}$ ions is characterized in that it comprises the steps consisting in:

(1°) preparing an aqueous solution of a silver component, which acts as a source of $Ag^+$ ions;

(2°) oxidizing at least some of the $Ag^+$ ions to $Ag^{2+}$ ions using persulfate, preferably with sodium persulfate $Na_2S_2O_8$ or ammonium persulfate $(NH_4)_2S_2O_8$, so as to obtain a redox potential of greater than or equal to 1000 mV, starting with 1 liter of demineralized water and 157 g of $AgNO_3$, and filtering to remove any insoluble material which may be present;

(3°) introducing the stabilizer into the resulting solution thus obtained;

(4°) introducing said resulting solution thus obtained into aqueous hydrogen peroxide solution or introducing the aqueous hydrogen peroxide solution into said resulting solution;

(5°) introducing into the resulting solution thus obtained an acidic substance which is $RCO_3H$, $RCO_2H$ or a mixture thereof $RCO_3H+RCO_2H$ in which R is defined as indicated above;

(6°) leaving the resulting solution thus obtained to stand until the equilibrium $H_2O_2+RCO_2H \Leftrightarrow H_2O+RCO_3H$ is established; and (7°) making up to 100% by weight with water.

When carrying out this process, $Ag^{3+}$ ions are liable to be obtained at least in trace amount.

According to the invention, a gelled composition (II) is also recommended, which is characterized in that it comprises:

the aqueous composition (I) mentioned above, and a gelling agent.

In practice, the gelled composition (II) will comprise 50% to 99.7% by weight of said aqueous composition (I) and 50% to 0.3% by weight of gelling agent. More specifically, the preferred gelling agent will be a pyrogenic colloidal silica or a compound of the polyacrylic type such as CARBOPOL® ETD 2623 from the company Goodrich, which is a copolymer of a $C_{10}$–$C_{30}$ alkyl acrylate, or CARBOPOL® 672 also from the company Goodrich, which is a polyacrylic homopolymer.

The process for preparing the gelled composition (II) consists (i) in placing said composition (I) in contact with the gelling agent, (ii) in stirring the resulting mixture for 3 to 20 minutes, and (iii) in leaving the resulting mixture to stand in order for it to set to a gel.

DETAILED DESCRIPTION OF THE INVENTION

In the text hereinbelow, except where otherwise mentioned, the respective amounts of the ingredients of the aqueous decontaminating composition according to the invention are expressed as percentages by weight, and the dilutions of said composition are expressed according to the ratio of the initial volume to the volume of the resulting dilute composition.

Hydrogen Peroxide

In general, the aqueous composition (I) according to the invention contains an $H_2O_2$ content which is less than or equal to 60% by weight relative to the weight of said composition. Thus, the composition (I) according to the invention may contain 0.1% to 60% by weight of $H_2O_2$ and may be diluted at the time of use (when the $H_2O_2$ concentration is greater than or equal to 4% by weight in particular.

In practice, since hydrogen peroxide raises transportation difficulties, when an aqueous hydrogen peroxide solution with an $H_2O_2$ content of greater than 8% by weight is used, especially with regard to the French and EC regulations, it would be advisable to provide an aqueous composition (I) containing not more than 8% by weight and better still not more than 7.9% by weight of $H_2O_2$.

Consequently, the aqueous composition (I) according to the invention will advantageously comprise an $H_2O_2$ content of about 7.5–7.9% by weight and will be diluted, at the time of use, with water in particular to a final $H_2O_2$ concentration of less than or equal to 4% by weight.

$RCO_2H/RCO_3H$ Mixture

With regard to the equilibrium reaction (4):

$$H_2O_2+RCO_2H \Leftrightarrow H_2O+RCO_3H \qquad (4)$$

the respective amounts of $RCO_3H$ and $RCO_2H$ in the mixture $RCO_3H/RCO_2H$ are not critical. It suffices to have in contact in $H_2O$ either $H_2O_2$ and $RCO_3H$ or $H_2O_2$ and $RCO_2H$ in order to obtain a ternary mixture $H_2O_2+RCO_3H+RCO_2H$ provided that $H_2O_2$ is in excess relative to the $RCO_2H/RCO_3H$ pair. Thus it suffices, as it were, to incorporate:

(i) $RCO_2H$ in the presence of $H_2O_2$, or (ii) $RCO_3H$ (which in concentrated form generally contains $H_2O_2$ and $RCO_2H$ according to documents FR-A-2 321 301 and FR-A-2 321 302 mentioned above), in $H_2O$, in order to obtain at equilibrium the combination $H_2O_2+RCO_3H+RCO_2H$.

As mentioned above, the group R of the acid/peracid pair represents a $C_1$–$C_6$ aliphatic residue containing a linear or branched, saturated or unsaturated hydrocarbon chain. Advantageously, use will be made of a group R containing a saturated linear hydrocarbon chain such as $CH_3$; $CH_3CH_2$ or $CH_3(CH_2)_4$ or alternatively of a group R containing an unsaturated linear hydrocarbon chain such as, in particular, $CH_3$—CH=CH, $CH_3$—CH=CH—$CH_2$ or $CH_3$—CH=CH—CH=CH.

The preferred groups R are (in order of increasing preference): $CH_3$—CH=CH—CH=CH, $CH_3CH_2$ or $CH_3$. In general, the pair CH$_3$CO$_2$H/CH$_3$CO$_3$H (i.e. R=methyl)

is preferred to the pair

CH$_3$CH$_2$CO$_2$H/CH$_3$CH$_2$CO$_3$H (i.e. R=ethyl)

since the first pair is more active than the second pair as a disinfecting/decontaminating means in the aqueous composition according to the invention.

Advantageously, in the aqueous composition (I) according to the invention, the weight ratio B/A of the mixture RCO$_2$H/RCO$_3$H to the hydrogen peroxide will be between 0.15/1 and 0.85/1. Preferably, this weight ratio will be between 0.5/1 and 0.7/1.

The Source L

The source L serves to provide the ions that are useful according to the invention, namely the ions containing the metal M (i.e. Ag$^{II}$, Ag$^{III}$, V$^V$, Nb$^V$, Ta$^V$, Mo$^{VI}$, W$^{VI}$, Co$^{III}$, In$^{III}$ or Tl$^{III}$ ions), the combination Ag$^+$/ions of the metal M, or mixtures thereof.

When V$^V$, Nb$^V$, Ta$^V$, Mo$^{VI}$, W$^{VI}$, Co$^{III}$, In$^{III}$ or Tl$^{III}$ ions are desired, use will be made of a source L which is a salt in which said metal M is in its maximum oxidation state. As a variant, a source L which may be used is an oxide of said metal M (in this case an oxide of V$^V$, Nb$^V$, Ta$^V$, Mo$^{VI}$, W$^{VI}$, Co$^{III}$, In$^{III}$ or Tl$^{III}$) if said oxide is soluble in acids.

When Ag$^{2+}$ ions are desired, the oxidation of Ag$^+$ (advantageously obtained from AgNO$_3$ or from colloidal silver) to Ag$^{2+}$ should be carried out.

The procedures recommended for the reaction Ag$^+$→Ag$^{2+}$+e are given later. Since this reaction is generally incomplete, it mainly gives a mixture of Ag$^+$/Ag$^{2+}$ ions [and, where appropriate, a mixture of Ag$^+$/Ag$^{2+}$/Ag$^{3+}$ ions in which the Ag$^{3+}$ ions are at least in trace amount].

When Ag$^+$ ions are desired in combination with V$^V$, Nb$^V$, Ta$^V$, Mo$^{VI}$, W$^{VI}$, Co$^{III}$, In$^{III}$ or Tl$^{III}$ ions, the ions obtained from the corresponding two sources are mixed together.

Finally, when an ionic mixture Ag$^+$/Ag$^{2+}$/V$^V$, Nb$^V$, Ta$^V$, Mo$^{VI}$, W$^{VI}$, Co$^{III}$, In$^{III}$ or Tl$^{III}$ ions is desired, the Ag$^+$/Ag$^{2+}$ ions obtained from their source by oxidation as indicated above are mixed with the ions from the abovementioned source of V$^V$, Nb$^V$, Ta$^V$, Mo$^{VI}$, W$^{VI}$, Co$^{III}$, In$^{III}$ or Tl$^{III}$ ions.

The preferred ions according to the invention comprise the V$^V$, Mo$^{VI}$, W$^{VI}$, and Tl$^{III}$ ions, on the one hand, and the ion mixtures Ag$^+$/Ag$^{2+}$, Ag$^+$/Mo$^{VI}$, Ag$^+$/W$^{VI}$, Ag$^+$/Tl$^{III}$ and Ag$^+$/Ag$^{2+}$/Mo$^{VI}$, on the other hand, the most advantageous ions being Ag$^+$/Ag$^{2+}$, Ag$^+$/Mo$^{VI}$, Ag$^+$/Ag$^{2+}$/Mo$^{VI}$ and above all the Mo$^{VI}$ ions.

It has been found, unexpectedly, during the use of the aqueous composition (I) according to the invention, that molybdenum has a twofold advantage over silver (in the form Ag$^+$ or Ag$^+$/Ag$^{2+}$):

as regards microorganisms, it is more active than silver, and during the cold sterilization of instruments (in particular dental or surgical instruments), it does not give the unattractive gray or black deposits of silver.

The main source of V$^V$ ions is a VO$_2^+$ (or, where appropriate, VO$_3^-$) salt, that of Nb$^V$ ions is an NbO$^{3+}$ salt, that of Mo$^{VI}$ ions is an MoO$_3^{2+}$ or MoO$_4^{2-}$ salt, that of Co$^{III}$ ions is a Co$^{3+}$ salt, that of W$^{VI}$ ions is a WO$_4^{2-}$ salt, that of Ta$^V$ ions is a Ta$^{5+}$ salt, that of In$^{III}$ ions is an In$^{3+}$ salt, and that of Tl$^{III}$ ions is a Tl$^{3+}$ salt.

The ions of the component C according to the invention act on microorganisms by making their wall brittle or by degrading it, on the one hand, and they also act as oxidizing means, in particular according to the following reactions, on the other hand:

VO$_2^+$+2H$^+$+$e$→VO$^{2+}$+H$_2$O or, where appropriate, (5)

VO$_3^-$+4H$^+$+$e$→VO$^{2+}$+2H$_2$O (5a)

Nb$^V$+$e\underline{2e}$→Nb$^{III}$ or (6)

NbO$^{3+}$+2H$^+$+$\underline{2e}$→Nb$^{3+}$+H$_2$O (6a)

MoO$_2^{2+}$+2H$^+$+$e$→MoO$^{3+}$+H$_2$O or (7)

MoO$_4^{2-}$+4H$^+$+$e$→MoO$_2^+$+2H$_2$O (7a)

Co$^{3+}$+$e$→Co$^{2+}$(in acidic medium) (8)

In$^{3-}$+2$e$→In$^+$ (9)

Tl$^{3+}$+2$e$→Tl$^+$. (10)

In practice, it is recommended as regards efficacy for the source L to be able to give, starting with an amount corresponding to 100 g of metal M and 1 liter of demineralized water, a resulting solution containing Ag$^{II}$, Ag$^{III}$, V$^V$, Nb$^V$, Ta$^V$, Mo$^{VI}$, W$^{VI}$, Co$^{III}$In$^{III}$ and/or Tl$^{III}$ ions with a redox potential of greater than 1 V.

Advantageously, the weight ratio of the source L of ions to the hydrogen peroxide will be between 0.0005/1 and 0.015/1. In practice, this weight ratio will be even more advantageously between 0.0008/1 and 0.005/1 and better still about 0.001/1.

The Stabilizer

The stabilizer, which protects H$_2$O$_2$ and the ions from the source L and which avoids any risk of explosion, in particular using concentrated solutions of (i) H$_2$O$_2$ and (ii) Ag$^+$ and/or Ag$^{2+}$, is chosen from the combination consisting of mineral acids such as H$_3$PO$_4$ and H$_2$SO$_4$ (nitric acid and hydrochloric acid being strongly advised against, in particular on account of their harmful effects on metal surfaces and/or the environment), on the one hand, and organic acids such as pyridinecarboxylic acids, on the other hand. The preferred stabilizer according to the invention is H$_3$PO$_4$ or (especially when the source L provides Mo$^{VI}$ ions) a pyridinecarboxylic acid.

Pyridinecarboxylic acids are substances of formula:

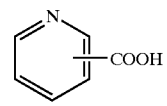

namely, 2-pyridinecarboxylic acid (picolinic acid), 3-pyridinecarboxylic acid (nicotinic acid) and 4-pyridinecarboxylic acid (isonicotinic acid).

When the source L of ions gives Ag$^+$ or Ag$^+$/Ag$^{2+}$ ions, it is advantageous to add, where appropriate, a small amount of gelatin to the acidic stabilizer of the component D.

Advantageously, the weight ratio of the stabilizer to the hydrogen peroxide will be between 0.0005/1 and 0.025/1. In practice, this weight ratio will be even more advantageously between 0.0008/1 and 0.005/1 and better still about 0.001/1.

The Other Additives

At least one of the following components may also be incorporated into the aqueous composition (I) according to the invention:

(E) wetting agent;

(F) anticorrosion agent; and (G) fragrance.

The wetting agent which is included herein is (i) an amphiphilic, amphoteric, anionic or nonionic surfactant compound, such as polyols that are suitable in particular for contact with foodstuffs and, where appropriate, suitable for oral administration with drinking water at the dose considered for use, or (ii) a mixture of such compounds. The product sold under the name Tegol® 2000 is suitable for this purpose as an amphoteric wetting agent.

In the aqueous composition (I) according to the invention, the weight ratio of the wetting agent to the hydrogen peroxide will advantageously be between 0.00005/1 and 0.01/1. In practice, this weight ratio will be even more advantageously about 0.005/1.

It is recommended to incorporate into the aqueous composition (I) according to the invention an anticorrosion agent which, at the dose used, is suitable for contact with foodstuffs and/or oral administration with drinking water. As anticorrosion agents which may be used for this purpose, mention may be made in particular of aminophosphonic acids as described in the abovementioned FR-A-2 321 302, the sodium, potassium, ammonium and alkanolamine salts thereof, and mixtures thereof. Hydroxyethanediphosphonic acid, dimethylaminomethanediphosphonic acid and ethylenediaminotetrakis(methylenephosphonic acid), the Na, K, $NH_4^+$ or alkanolamine salts thereof, and mixtures thereof, are particularly suitable for the aqueous composition (I) according to the invention. 1,2,3-Benzotriazole is also suitable as an anticorrosion agent.

In practice, the anticorrosion agent will be present in the aqueous composition (I) at low concentration. If it is used, said anticorrosion agent will be included especially in an amount such that the weight ratio of said anticorrosion agent to the hydrogen peroxide is between 0.00005/1 and 0.03/1 and preferably between 0.001/1 and 0.005/1.

As indicated in WO-A-96/18301, it is prudent to limit the corrosion of metal surfaces (mainly made of iron or copper) in very prolonged contact with the aqueous composition (I) of the invention to a value of less than 200 $\mu$m/year.

As the corrosion of metal surfaces is mainly reflected by a phenomenon known as "pitting", it is appropriate to avoid the formation of said pitting in which the microorganisms which it is desired to irradicate would live and grow.

The fragrance component in point (G) will be included in the aqueous decontaminating composition in an amount of less than or equal to that of the anticorrosion agent in point (F).

The water which is included in the decontaminating composition according to the invention is advantageously a purified water, namely distilled water, demineralized water or, better still, deionized water. Preferably, the deionized water used herein will be a water with a resistivity of greater than $10^5$ $\Omega$/cm and better still greater than or equal to $10^6$ $\Omega$/cm.

The water used for any diluting of said decontaminating composition according to the invention will advantageously be purified water as indicated above.

The pH of the aqueous composition according to the invention is (before dilution and then use) generally between 1.2 and 5 and better still between 1.5 and 4. It is adjusted by means of the preferred component D: $H_3PO_4$ or pyridinecarboxylic acid.

The Aqueous Composition (I)

Preferably, the aqueous composition (I) according to the invention, with regard to the foregoing text, contains, in water:

(A) not more than 8% by weight of $H_2O_2$;
(B) a mixture $RCO_2H/RCO_3H$ (in which R is $CH_3$ or $CH_3CH_2$), in a weight ratio of said mixture $RCO_2H/RCO_3H$ to hydrogen peroxide of from 0.15/1 to 0.85/1 and preferably from 0.5/1 to 0.7/1;

(C) a source L providing metal ions chosen from the combination consisting of:
(1) ions of a metal M which are $Ag^{II}$, $Ag^{III}$, $V^V$, $Nb^V$, $Ta^V$, $Mo^{VI}$, $W^{VI}$, $Co^{III}$, $In^{III}$ or $Tl^{III}$ ions,
(2) combinations of $Ag^+$ ions and of ions of said metal M, and
(3) mixtures thereof,
the source L, which gives $Ag^{II}$ ions or $Ag^{II}+Ag^{III}$ ions, being such that, starting with 100 g of silver (i.e. 157 g of $AgNO_3$) and 1 liter of demineralized water, the concentration of $Ag^++Ag^{2+}$ or $Ag^++Ag^{2+}+Ag^{3+}$ ions in the resulting solution gives a redox potential of greater than 1000 mV;
according to a weight ratio of said source L to hydrogen peroxide of from 0.0005/1 to 0.015/1 and preferably from 0.0008/1 to 0.005/1; and
(D) a stabilizer, in a weight ratio of said stabilizer to hydrogen peroxide of from 0.0005/1 to 0.015/1 and preferably from 0.0008/1 to 0.005/1.

Even more practically, a standard composition (i.e. a stock composition) which is intended to be diluted at the time of use is recommended. This standard composition contains:

(A) 7.5–7.9% by weight of $H_2O_2$;
(B) 4.5% to 4.8% by weight of a mixture $CH_3CO_3H+CH_3CO_2H$;
(C) 0.005% to 0.01% by weight of the source L;
(D) 0.0005% to 0.01% by weight of $H_3PO_4$ or of pyridinecarboxylic acid;
(E) where appropriate, 0.0075% to 0.04% by weight of surfactant;
(F) where appropriate, 0.003% to 0.04% by weight of anticorrosion agent;
(G) where appropriate, a fragrance; and
water (distilled, demineralized or deionized) to make up to 100% by weight.

It may be advantageous, in particular in the context of the cleaning, stripping and/or passivation treatment of a metal surface or in the context of the cleaning and/or stripping treatment of a nonmetal surface, for the weight ratio C/D to be less than 1/1.

Moreover, when the component C is a mixture of $Ag^+$ ions and of M ions, it suffices, according to the invention, for the metal ions of M to be in trace amount in order for the beneficial effects to be manifested.

Preparation of the Composition (I)

The process for preparing the aqueous composition (I) according to the invention, which is given above and comprises steps (a)–(f), is carried out directly when the source L contains no $Ag^{2+}$ (or $Ag^{2+}/Ag^{3+}$) ions. In this case, said composition may be produced according to the teaching of GB-A-2 189 394 (in order to obtain a high concentration of $H_2O_2$), on the one hand, and then by diluting (for an $H_2O_2$ concentration of less than or equal to 8% by weight and better still less than or equal to 7.9% by weight) with distilled, demineralized or deionized water for the purpose of transportation, on the other hand. As a variant, said composition may be produced directly in the form of a standard composition.

When the source L gives $Ag^{2+}$ (or $Ag^{2+}/Ag^{3+}$) ions, step (a) is then replaced with steps (1°) and (2°) to make use of a source of $Ag^+$ ions, which are oxidized to $Ag^{2+}$ ions. This oxidation is carried out (i) using a persulfate, preferably sodium persulfate or ammonium persulfate, as oxidizing agent, and (ii) in the absence of white light to avoid the UV-mediated reduction of the silver ions to metallic silver which precipitates in situ. The oxidation $Ag^+ \rightarrow Ag^{2+}+e$ will advantageously be performed in darkness (i.e. in opaque reactors) or in red light.

The filtration included at the end of step (2°) has the purpose of removing any insoluble material which may be present in the reaction medium. The presence of an insoluble material is mainly manifested when the persulfate used is ammonium persulfate. Advantageously, this filtration is carried out using a filter membrane having pores with a diameter of about 3 μm.

In step (3°)—i.e. step (b) of the general process—the silver ions obtained (generally a mixture of $Ag^+$, $Ag^{2+}$ and, where appropriate, $Ag^{3+}$) are preferably stabilized using $H_3PO_4$ (as an aqueous solution at 70–85% by weight) or using a pyridinecarboxylic acid.

Even more advantageously, a small amount of gelatin will be added before, during or after the addition of $H_3PO_4$ or of a pyridinecarboxylic acid.

As indicated above, if it contains $Ag^{2+}$ or $Ag^{2+}+Ag^{3+}$ ions, the aqueous composition according to the invention may be produced either in the form of a standard solution or in the form of a solution with a high $H_2O_2$ content before dilution for transportation.

One of the preferred modes (mode A) for carrying out the process for preparing the composition (I) according to the invention, when the source L gives $V^V$, $Nb^V$, $Ta^V$, $Mo^{VI}$, $W^{VI}$, $Co^{III}$, $In^{III}$ or $Tl^{III}$ ions, comprises the following steps (for the production of a standard composition containing 7.5–7.9% by weight of $H_2O_2$) consisting in:

(a) preparing a solution of a $V^V$, $Nb^V$, $Ta^V$, $Mo^{VI}$, $W^{VI}$, $Co^{III}$, $In^{III}$ or $Tl^{III}$ salt (advantageously in acidic medium) in a portion of the total amount of water required to prepare said aqueous disinfecting composition;

(b) introducing into the resulting solution thus obtained an aqueous phosphoric acid solution containing 70% to 85% by weight of $H_3PO_4$ or an aqueous pyridinecarboxylic acid solution;

(c) introducing the resulting solution thus obtained into an aqueous hydrogen peroxide solution containing 50% to 60% by weight of $H_2O_2$, with stirring, at a temperature of between 0° C. and 25° C. (preferably at a temperature of between 4° C. and 15° C.), and with a rate of introduction of the solution obtained in step (b) of between 3 and 6 l/h;

(d) introducing into the resulting solution thus obtained the acidic substance $CH_3CO_2H$, with stirring, at a temperature of between 0° C. and 25° C. (preferably at a temperature of between 4° C. and 15° C.) and with a rate of introduction of the acidic substance $CH_3CO_2H$ of between 3 and 6 l/h;

(e) leaving the resulting solution thus obtained to stand for 48 hours (preferably in darkness), at a temperature of between 0° C. and 25° C. (preferably at a temperature of between 4° C. and 15° C.), in order for the equilibrium

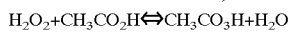

to be established, and (f) adding the remaining water to make up to 100% by weight.

In step (d) of the preparation of this composition, the acid $CH_3CO_2H$ may be introduced in the form of an aqueous solution.

Another preferred mode (mode B) for carrying out the process for preparing the composition (I) according to the invention, when the source L provides $Ag^{2+}$ ions (with, where appropriate, $Ag^{3+}$ ions) comprises the following steps (for the production of a standard composition containing 7.5–7.9% by weight of $H_2O_2$) consisting in:

(1°) dissolving $AgNO_3$ in demineralized water with a resistivity of $10^6$ Ω/cm (in a proportion of 157 g of silver nitrate—i.e. 100 g of silver—to 1 liter of demineralized water), the redox potential of the solution thus obtained being about 600 mV;

(2°) oxidizing at least a portion of the $Ag^+$ ions of the above solution to $Ag^{2+}$ or to $Ag^{2+}+Ag^{3+}$ by addition of sodium persulfate or ammonium persulfate, so as to obtain a redox potential of greater than or equal to 1000 mV (in particular a redox potential of greater than or equal to 1600 mV); filtering (on a membrane with pores 3 μm in diameter);

(3°) stabilizing the resulting solution thus obtained using an aqueous phosphoric acid solution containing 70% to 85% by weight of $H_3PO_4$ [in a proportion of from 10 to 100 ml of aqueous $H_3PO_4$ solution at 70% to 85% by weight per 1 liter of demineralized water used in step (1°)] or using an aqueous pyridinecarboxylic acid solution [after stirring for 24 hours at room temperature, the solution of silver ions thus stabilized having a redox potential of greater than or equal to 1000 mV];

(4°) introducing the resulting solution thus obtained into an aqueous hydrogen peroxide solution containing 50% to 60% by weight of $H_2O_2$, with stirring, at a temperature of between 0° C. and 25° C. (preferably at a temperature of between 4° C. and 15° C.), and with a rate of introduction of the solution obtained in step (3°) of between 3 and 6 l/h;

(5°) introducing into the resulting solution thus obtained the acidic substance $CH_3CO_2H$, with stirring, at a temperature of between 0° C. and 25° C. (preferably at a temperature of between 4° C. and 15° C.), and with a rate of introduction of the acidic substance $CH_3CO_2H$ of between 3 and 6 l/h;

(6°) leaving the resulting solution thus obtained to stand for 48 hours, in darkness (or in red light) at a temperature of between 0° C. and 25° C. (preferably at a temperature of between 4° C. and 15° C.), in order for the equilibrium

to be established, and (7°) adding water to make up to 100% by weight.

In step (5°) of the preparation of this standard composition, the acid $CH_3CO_2H$ may be introduced in the form of an aqueous solution.

The Gelled Composition (II)

The gelled composition (II) in accordance with the invention is obtained using the aqueous composition (I) and a specific gelling agent, which is a mineral substance or an organic substance. When this gelling agent is a mineral substance, it is advantageously pyrogenic colloidal silica which is, in dry form, in the form of particles with an area per unit mass of from 80 to 400 m²/g and a mean particle size of from 7 to 20 nm. Among the silicas which are suitable for this purpose, mention may be made in particular of those sold by the company Cabot under the name CAB-O-SIL®, and in particular the products CAB-O-SIL® LM-150, CAB-O-SIL® M-5, CAB-O-SIL® EH-5 and CAB-O-SIL® M-7D, which are hydrophilic.

In order to produce a gelled composition (100 parts by weight) containing pyrogenic silica, the process is performed as follows:

placing composition (I) (50 to 99 parts by weight) and the pyrogenic colloidal silica (50 to 1 parts by weight) in contact, stirring for 3–10 minutes with an angular speed of the stirrer of from 1500 to 2000 rpm, and then leaving to stand at room temperature.

When the gelling agent is an organic substance, it is advantageously a polyacrylic material as indicated above. In this case, the gelled composition (100 parts by weight) which contains said polyacrylic material will be prepared as follows:

placing the composition (I) (90 to 99.7 parts by weight) and the organic gelling material (10 to 0.3 parts by weight) in contact, stirring for 10–20 minutes with an angular speed of the stirrer of from 1000 to 2000 rpm, and then leaving to stand at room temperature.

The gelled composition (II) containing a polyacrylic organic gelling material can be used only at a pH of greater than or equal to 3.5; in practice, it will be used at a pH of from 3.5 to 7 and preferably at pH 5. Moreover, it is suitable for the preparation of transparent gels that are valued by the public in dermatology and in cosmetology.

On the other hand, the gelled composition (II) containing pyrogenic silica will advantageously be used at a pH of from 1.5 to 4.

The gel obtained has thixotropic properties: it becomes fluid under a stress such as stirring, friction or shear and sets to a solid quickly (in less than 5 minutes) when the stirring, friction or shear stops.

Moreover, this gel is stable in acidic or weakly alkaline medium; it is also stable up to the degradation temperature of its constituents.

Depending on the water content, said gel may be prepared in a wide range of viscosities.

On account of its thixotropic properties, the gelled composition (II) according to the invention is particularly suitable for decontaminating aged oils and greases (which are the nutrient media of several microorganisms liable to be pathogenic) in situ in industrial plants and devices.

The Uses

The uses of the aqueous oxidizing composition (I) according to the invention comprise (i) those envisaged in the abovementioned publication WO-A-96/18301 (see page 20, line 11 to page 22, line 15) in particular as regards the disinfection of water to make it fit for drinking, the hygiene of industrial premises and swimming pools, the cold sterilization of surgical and dental instruments, the protection of plants and crops against bacteria, molds, viruses and parasites, the protection of fish, crustaceans and shellfish against pathogenic algae such as Euglena, and the decontamination of mining sites, and (ii) the novel uses which relate to the cleaning, stripping and/or passivation of metal surfaces (in particular surfaces made of steel or aluminum) or nonmetal surfaces (in particular plastic or ceramic surfaces, the plastic surfaces comprising herein those of floor-covering or wall panels which are exposed and which are generally made of PVC, polyacrylate, polycarbonate or the like).

Advantageously, the composition (I) intended for disinfection and hygiene will be obtained by diluting a standard composition so as to have an $H_2O_2$ concentration of from 1% to 2% by weight.

Also advantageously, the composition (I) intended for decontaminating mining sites will have an $H_2O_2$ content of from 4% to 7.9% by weight and will be diluted at the time of use to a final working concentration of less than or equal to 1/100 (i.e. a final $H_2O_2$ content of less than or equal to 0.04% by weight).

In the field of treating surfaces, the composition (I) will advantageously have an $H_2O_2$ content of between 1% and 7.9% by weight and will comprise a weight ratio C/D of less than 1/1 and greater than 1/2.

The gelled composition (II) according to the invention offers the advantage of providing, in the region of the article or surface to be treated, a source of $H_2O_2$ and of ions originating from L which is stabilized and which ensures long-lasting action.

The gelled composition (II) is particularly useful with regard to surfaces that are not horizontal, i.e. vertical, curved or inclined surfaces. It is most particularly suitable for protecting constructions against microorganisms liable to grow in the cavities of the outer walls of buildings exposed to dust and to bird droppings, on the one hand, and for stripping and passivating metal reactors or tanks, on the other hand.

The gelled composition II is thus recommended according to the invention for use, on the one hand, as a germicidal product for p reparing a medicinal product intended for therapeutic use with regard to oral conditions, in particular of the periodontium, caused by bacteria and/or fungi, and, on the other hand, as a cosmetic product, in p articular in the form of a toothpaste, for oral hygiene.

In the dental field, it has been found that the gelled composition (II) serves as a hemostatic agent, dispenses with the administration of antibacterial and/or antifungal agents, inhibits catalase and ensures the passivation of the metal surfaces of bridges (said passivation preventing the deposition of bacteria and fungi over a long period of time), and also the temporary protection of plastic or ceramic surfaces against said bacteria and fungi (their deposition thus being prevented). This gelled composition is suitable for preparing toothpastes containing 1% to 2% by weight of hydrogen peroxide.

Other advantages and characteristics of the invention will emerge more clearly on reading the embodiments and comparative tests which follow. Needless to say, this set of data is not limiting in any way, but is given for illustrative purposes. For convenience, where the component (C) is concerned, the source of ions L, its proportion by weight and the ions it gives are indicated below in Ex. 1–Ex. 6.

EXAMPLE 1

A standard composition is prepared according to mode A given above, containing:

| | |
|---|---|
| $H_2O_2$ | 7.8% by weight |
| $CH_3CO_2H + CH_3CO_3H$ mixture | 4.8% by weight |
| $Na_2MoO_4$(source of $MoO_4^{2-}$) | 0.008% by weight |
| Pyridinecarboxylic acid | 0.008% by weight |
| Surfactant (anionic wetting agent) | 0.04% by weight |
| $H_2O$ (demineralized) to make up to | 100% by weight |

EXAMPLE 2

A standard composition is prepared according to mode A given above, containing:

When the source of ions L gives $Mo^{VI}$ ions, it is important not to use $H_3PO_4$ as stabilizer. It should be avoided to place $H_3PO_4$ in contact with $MoO_4^{2-}$, as this would give a complex of the phosphonomolybdate type which is insoluble.

EXAMPLE 3

A standard composition is prepared according to mode A given above, containing:

| | |
|---|---|
| $H_2O_2$ | 7.8% by weight |
| $CH_3CO_2H + CH_3CO_3H$ mixture | 4.8% by weight |
| $NH_4VO_3$ (source of $VO_3^-$, $VO_2^+$ or $V^{5+}$) | 0.008% by weight |
| $H_3PO_4$ or pyridinecarboxylic acid | 0.008% by weight |
| Surfactant (anionic wetting agent) | 0.04% by weight |
| $H_2O$ (demineralized) to make up to | 100% by weight |

EXAMPLE 4

A standard composition is prepared according to mode A given above, containing:

| | |
|---|---|
| $H_2O_2$ | 7.8% by weight |
| $CH_3CO_2H + CH_3CO_3H$ mixture | 4.8% by weight |
| $Na_2WO_4$ (source of $WO_4^{2-}$) | 0.008% by weight |
| $H_3PO_4$ or pyridinecarboxylic acid | 0.008% by weight |
| Surfactant (anionic wetting agent) | 0.04% by weight |
| $H_2O$ (demineralized) to make up to | 100% by weight |

EXAMPLE 5

The standard composition of Example 5 is prepared from a 1/1 mixture by weight of the compositions of Examples 1 and 2. This standard composition contains:

| | |
|---|---|
| $H_2O_2$ | 7.8% by weight |
| $CH_3CO_2H + CH_3CO_3H$ mixture | 4.8% by weight |
| $AgNO_3$ (source of $Ag^+/Ag^{2+}$) | 0.004% by weight |
| $Na_2MoO_4$ (source of $MoO_4^{2-}$) | 0.004% by weight |
| Pyridinecarboxylic acid | 0.008% by weight |
| Surfactant (anionic wetting agent) | 0.04% by weight |
| $H_2O$ (demineralized) to make up to | 100% by weight |

Comparative Example CP1

The composition of Example 1 of prior art document WO-A-96/18301 is used as comparative product. Its formulation is as follows:

| | |
|---|---|
| $H_2O_2$ | 8% by weight |
| $CH_3CO_2H + CH_3CO_3H$ mixture | 4.8% by weight |
| $AgNO_3$ (source of $Ag^+$) | 0.008% by weight |
| $H_3PO_4$ | 0.008% by weight |
| Surfactant (anionic wetting agent) | 0.04% by weight |
| $H_2O$ (demineralized) to make up to | 100% by weight |

EXAMPLE 6

Starting with a 1/1 mixture by weight of the compositions of Ex. 2 and CP1, a standard composition is obtained (after replacing the phosphoric acid in CP1 with a pyridinecarboxylic acid), having the formulation:

| | |
|---|---|
| $H_2O_2$ | 7.9% by weight |
| $CH_3CO_2H + CH_3CO_3H$ mixture | 4.8% by weight |
| $AgNO_3$ (source of $Ag^+$) | 0.004% by weight |
| $Na_2MoO_4$ (source of $MoO_4^{2-}$) | 0.004% by weight |
| Pyridinecarboxylic acid | 0.008% by weight |
| Surfactant (anionic wetting agent) | 0.04% by weight |
| $H_2O$ (demineralized) to make up to | 100% by weight |

Comparative Tests I

The germicidal activity of Ex.1–Ex. 6 and CP1 was determined with respect to three bacterial strains (1–3) and one strain of mold (4) which are pathogenic to man (1-2) or phytopathogenic (3-4), especially for tomatoes grown in the open air, namely:

(1) *Staphylococcus aureus*

(2) *Pseudomonas aerugina,*

(3) *Pseudomonas syringea,* and (4) *Alternaria solani.*

If $[S]_0$ is the concentration of a strain S at time 0 and $[S]_T$ is the concentration of the same strain at the time T (T=1 hour for bacteria and T=2 hours for molds), the germicidal activity is measured by the difference:

$$\Delta = \log[S]_0 - \log[S]_T$$

a product being active when it reduces the number of live strains such that $\Delta \geq 4$ for bacteria and $\Delta \geq 3$ for molds.

The results obtained for $\Delta$ given in Table I below show that CP1 at a dilution of 1/5 is effective with respect to bacteria but is virtually lacking in activity on the strain of *Alternaria solani*. These results also show that, at the same dilution of 1/5, Ex. 1–Ex. 6 are (i) effective on bacteria and molds, and (ii) more active than CP1.

EXAMPLE 7

10 g of CAB-O-SIL® M-5 pyrogenic silica are added with vigorous stirring (2000 rpm) to one liter of the aqueous composition of Ex. 1 over 6 minutes. The mixture is left to stand and a gel with a viscosity of $10^6$ Pa.s is obtained.

Comparative Tests II

The action of the aqueous composition CP1 was compared with the gel of Ex. 7. The two products were applied for 4 hours to a roof made of anodized aluminum alloy with a westerly aspect and coated with mosses and lichens. The treatment with CP1 was found to be ineffective on account of the insufficient contact time due to the evaporation of the solution. On the other hand, all of the mosses and lichens were removed by a simple rinsing with running water after the 4 hours of the experiment.

EXAMPLE 8

100 g of CAB-O-SIL® M-5 pyrogenic silica and 500 ml of aqueous phosphoric acid solution containing 75% by weight of $H_3PO_4$ are added with vigorous stirring (2000 rpm) to one liter of the aqueous composition of Ex. 1, over 6 minutes. The mixture is left to stand and a gel with a viscosity of $10^7$ Pa.s is obtained.

The gel thus obtained is highly thixotropic.

Tests III

The gel of Ex. 8, applied to an industrial kitchen extractor hood made of 316L stainless steel depassivated after a fire which released chlorine-rich vapors, and left in contact for 3 hours, allowed the 316L stainless steel to be completely decontaminated and to regain its passivity potential.

EXAMPLE 9

The aqueous composition of Ex. 1 is diluted with demineralized water so as to obtain an $H_2O_2$ content of 1% to 2% by weight. The resulting solution is then gelled according to the process of Example 7 above.

Tests IV

The gel of Ex. 9 was applied once a day for 5 days to the teeth and the mucosa of the periodontium in the region of the teeth, to patients suffering from dental plaque and/or oral mycosis, and who had bad breath. Biopsies of the mucosa of the periodontium showed a total reduction in situ in the bacteria and fungi responsible for the dental plaque and the mycoses, respectively. The treated patients no longer had bad breath.

EXAMPLE 10

The aqueous composition of Ex. 1 is diluted with demineralized water so as to obtain an $H_2O_2$ content of 4% by weight. The resulting solution is then gelled according to the process of Example 8 above.

Tests V

The gel of Ex. 10 was applied to stainless steel tanks used for manufacturing champagne. Statistically, it is known that the contents of one tank in every five or six is lost due to (i) the growth of inappropriate microorganisms and/or (ii) the degradation of the inner wall. By treating the inner wall of the tanks for 5 hours with the gel of Ex. 10 followed by rinsing with water, once before the grape harvesting and once after emptying the tanks following fermentation, all the tanks are kept active while avoiding the conventional loss mentioned above.

Tests VI

Each of the compositions of Ex. 1, Ex. 2, Ex. 5 and CP1 is diluted extemporaneously (i.e. at the time of use) so as to obtain a dilution of 1/5. 50 ml of each of the solutions thus diluted are placed in batches of transparent glass containers and, at time T=0, a dental prosthesis, which (a) comprises metal, plastic and/or ceramic surfaces, (b) is infested with bacteria and/or molds, and (c) is soiled with traces of tissues (coagulated blood, mucosa, flesh) and adhesive, is immersed in these solutions. The open containers are left to stand. The prostheses in the batches of containers are observed at times T=1 hour, T=2 hours, T=15 days and T=90 days.

It is found that, at T=1 hour, the prostheses immersed in the dilute compositions of Ex. 1, Ex. 2 and Ex. 5 are clean and essentially free of bacteria and molds; at T=2 hours, the prostheses immersed in the dilute compositions of Ex. 1, Ex. 2 and Ex. 5 are clean and essentially free of bacteria and molds, and the prostheses immersed in the dilute composition of CP1 are clean, free of bacteria, but are still contaminated with molds (population$\geq 10^4$ microorganisms/ml; at T=15 days, all the prostheses are clean and free of bacteria, those immersed in the dilute composition of CP1 having a mold population of greater than $10^4$ microorganisms/ml, whereas those treated with the dilutions of Ex. 1, Ex. 2 and Ex. 5 are free of molds; at T=90 days, only the prostheses treated with the dilutions of Ex. 1, Ex. 2 and Ex. 5 are clean and free of bacteria and molds, those treated with the dilution of CP1 are again contaminated with bacteria and molds.

In brief, after treatment for one hour with Ex. 1, Ex. 2 and Ex. 5, each prosthesis is considered as "being entirely new and reusable". It is moreover found that, unlike CP1, Ex. 1, Ex. 2 and Ex. 5 prevent the bacteria and molds from attaching to a surface.

TABLE I

| | Germicidal activity $\Delta = \log [S]_0 - \log [S]_T$ | | | |
|---|---|---|---|---|
| | Strains | | | |
| Product | (a) | (b) | (c) | (d) |
| CP1 | 4.56 | 5.38 | 3.97 | 1.61 |
| Ex. 1 | 6.27 | 6.14 | 5.23 | 4.42 |
| Ex. 2 | 6.25 | 6.17 | 5.25 | 4.44 |
| Ex. 3 | 5.0 | 5.19 | 4.67 | 4.45 |
| Ex. 4 | 6.27 | 5.17 | 5.30 | 4.43 |
| Ex. 5 | 6.25 | 5.67 | 5.27 | 4.42 |
| Ex. 6 | 5.37 | 5.70 | 5.27 | 4.42 |

Notes:
(a) *Staphylococcus aureus*
(b) *Pseudomonas aerugina*
(c) *Pseudomonas syringae*
(d) *Alternaria solani*

EXAMPLE 11

A dermatological or cosmetic composition is prepared using the following formulation:

| | |
|---|---|
| $H_2O_2$ | 1 part by weight |
| $CH_3CO_2H + CH_3CO_3H$ mixture | 0.5 part by weight |
| $CH_3$-CH=CH—CH=CH—$CO_2H$ | 0.1 part by weight |
| Pyridinecarboxylic acid | 0.004 part by weight |
| $Na_2MoO_4$ (source of $MoO_4^{2-}$) | 0.004 part by weight |
| Surfactant (nonionic wetting agent) | 0.02 part by weight |
| $H_2O$ (demineralized) to make up to | 95.5 parts by weight |

The ingredients are introduced into a portion of the demineralized water required, in the following order: (i) $H_2O_2$, (ii) $CH_3CO_2H/CH_3CO_3H+CH_3$—CH=CH—CH=CH—$CO_2H$+pyridinecarboxylic acid, (iii) $Na_2MoO_4$, and then (iv) demineralized water up to a total weight of 95.5 parts by weight.

EXAMPLE 12

A gelled composition containing a polyacrylic organic material as gelling agent is prepared using the following formulation:

| | |
|---|---|
| $H_2O_2$ | 1% by weight |
| $CH_3CO_2H + CH_3CO_3H$ mixture | 0.5% by weight |
| $CH_3$-CH=CH—CH=CH—$CO_2H$ | 0.1% by weight |
| Pyridinecarboxylic acid | 0.004% by weight |
| $Na_2MoO_4$ (source of $MoO_4^{2-}$) | 0.004% by weight |
| NaOH (up to pH 5) | |
| Surfactant (nonionic wetting agent) | 1% by weight |
| CARBOPOL ® ETD 2623 | 0.5% by weight |
| $H_2O$ (demineralized) to make up to | 100% by weight |

This composition is prepared by stirring (at 800–1000 rpm) CARBOPOL® 2623 in a portion of the demineralized water required, maintaining this stirring for 15 minutes, heating to 45° C. until completely dissolved, adding, in the following order, (i) $H_2O_2$, (ii) $CH_3CO_2H/CH_3CO_3H$, $CH_3$—CH=CH—CH=CH—$CO_2H$ and then pyridinecarboxylic acid, and (III) $Na_2MoO_4$ followed by surfactant, stirring for 15 minutes (at 1000 rpm), adjusting the pH to 5 with NaOH, and (iv) demineralized water up to 100% by weight. The Brookfield viscosity at 20 rpm of this gelled composition is 15 Pa.s (i.e. 15000 cP).

What is claimed is:

1. An aqueous oxidizing composition (I) which is useful in the field of disinfection, hygiene and decontamination, and in the field of treating, cleaning, stripping and/or passivating surfaces, said composition, which comprises, in water, hydrogen peroxide, an $RCO_2H/RCO_3H$ mixture in which R is a $C_1$–$C_6$ aliphatic residue containing a linear or branched, saturated or unsaturated hydrocarbon-based chain, and a stabilizer which is an acid and, optionally, $Ag^+$ ions, being characterized in that it contains ions of at least one metal M selected from the group consisting of $Ag^{II}$, $Ag^{III}$, $V^V$, $Nb^V$, $Ta^V$, $Mo^{VI}$, $W^{VI}$, $Co^{III}$, $In^{III}$ and $Tl^{III}$ ions, the source L of the metal M, which gives $Ag^{II}$ ions or $Ag^{II}+Ag^{III}$ ions, wherein starting with 100 g of silver and 1 liter of demineralized water, the concentration of $Ag^++Ag^{2+}$ or $Ag^++Ag^{2+}+Ag^{3+}$ ions in the resulting solution gives a redox potential of greater than 1,000 mV.

2. The composition as claimed in claim 1, characterized in that the metal ions from source L are selected from the group consisting of:
   (1) ions of a metal M selected from the group consisting of $Ag^{II}$, $Ag^{III}$, $V^V$, $Nb^V$, $Ta^V$, $Mo^{VI}$, $W^{VI}$, $Co^{III}$, $In^{III}$ or $Tl^{III}$ ions,
   (2) combinations of $Ag^+$ ions and of ions of said metal M, and
   (3) mixtures thereof.

3. The composition as claimed in claim 2, characterized in that said metal ions are $Mo^{VI}$ ions, a mixture of $Ag^+/Ag^{2+}$ ions, a mixture of $Mo^{VI}/Ag^+$ ions or a mixture of $Mo^{VI}/Ag^+/Ag^{2+}$ ions.

4. The composition as claimed in claim 1, characterized in that it is in the form of a gelled composition (II) which further comprises a mineral or organic gelling agent.

5. The composition as claimed in claim 4, characterized in that it comprises:
   (a) 50% to 99% by weight of the aqueous composition (I) as claimed in claim 1, and
   (b) 50% to 1% by weight of pyrogenic colloidal silica with an area per unit mass of from 80 to 400 m²/g and a mean particle size of from 7 to 20 nm, as gelling agent.

6. The composition as claimed in claim 4, characterized in that it comprises:
   (a) 90% to 99.7% by weight of the aqueous composition (I) as claimed in claim 1, and
   (b) 10% to 0.3% by weight of a polyacrylic organic material as gelling agent.

7. The gelled composition as claimed in claim 4, characterized in that said gelled composition is incorporated in a germicidal product for preparing a medicinal product intended for use with regard to oral conditions.

8. The gelled composition as claimed in claim 4, characterized in that said gelled composition is incorporated in a cosmetic product for oral hygiene.

9. The gelled composition as claimed in claim 4, characterized in that said gelled composition is incorporated in a composition (i) for cleaning, stripping or passivating a metal surface, or (ii) for cleaning or stripping a nonmetal surface.

10. A process for preparing the gelled composition (II) as claimed in claim 4, said process being characterized in (i) placing said composition (I) in contact with a gelling agent, (ii) stirring the resulting mixture for 3 to 20 minutes, and (iii) allowing the resulting mixture to stand in order for it to set to a solid.

11. A process for preparing an aqueous composition as claimed in claim 1, said process being characterized in
   (a) providing an aqueous solution of a source L giving metal ions selected from the group consisting of
      (1) ions of a metal M selected from the group consisting of $Ag^{II}$, $Ag^{III}$, $V^V$, $Nb^V$, $Ta^V$, $Mo^{VI}$, $W^{VI}$, $In^{III}$ or $Tl^{III}$ ions,
      (2) combinations of $Ag^+$ ions and of ions of said metal M, and
      (3) mixtures thereof;
         the source L, which gives $Ag^{II}$ ions or $Ag^{II}+Ag^{III}$ ions, being such that, starting with 100 g of silver and 1 liter of demineralized water, the concentration of $Ag^++Ag^{2+}$ or $Ag^++Ag^{2+}+Ag^{3+}$ ions in the resulting solution gives a redox potential of greater than 1,000 mV;
   (b) introducing a stabilizer into said solution;
   (c) combining the resulting solution thus obtained with an aqueous hydrogen peroxide solution;
   (d) introducing into the resulting solution thus obtained an acidic substance which is $RCO_3H$, $RCO_2H$ or a mixture thereof;
   (e) allowing the resulting solution thus obtained to stand until the equilibrium $H_2O_2+RCO_2H \Leftrightarrow H_2O+RCO_3H$ is established; and
   (f) adding water to the solution.

12. The process as claimed in claim 11, for preparing a composition which contains $Ag^{2+}$ ions, said process being characterized in that it comprises
   (1) preparing an aqueous solution of a silver component, which acts as a source of $Ag^+$ ions;
   (2) oxidizing at least some of the $Ag^+$ ions to $Ag^{2+}$ or $Ag^{2+}+Ag^{3+}$ ions using persulfate, so as to obtain a redox potential of greater than or equal to 1,000 mV, and filtering to remove insoluble material which may be present;
   (3) introducing the stabilizer into the resulting solution thus obtained;
   (4) combining said resulting solution thus obtained with an aqueous hydrogen peroxide solution;
   (5) introducing into the resulting solution thus obtained an acidic substance which is $RCO_3H$, $RCO_2H$ or a mixture thereof;
   (6) allowing the resulting solution thus obtained to stand until the equilibrium $H_2O_2+RCO_2H \Leftrightarrow H_2O+RCO_3H$ is established; and
   (7) adding water to the resulting solution.

* * * * *